(12) United States Patent
Miyoshi et al.

(10) Patent No.: US 11,461,892 B2
(45) Date of Patent: Oct. 4, 2022

(54) CELL OBSERVATION SYSTEM

(71) Applicant: EVIDENT CORPORATION, Nagano (JP)

(72) Inventors: Takashi Miyoshi, Kanagawa (JP); Shinichi Takimoto, Tokyo (JP); Yasunobu Iga, Tokyo (JP); Shintaro Takahashi, Tokyo (JP)

(73) Assignee: Evident Corporation, Nagano (JP)

( * ) Notice: Subject to any disclaimer, the term of this patent is extended or adjusted under 35 U.S.C. 154(b) by 252 days.

(21) Appl. No.: 16/724,375

(22) Filed: Dec. 22, 2019

(65) Prior Publication Data

US 2020/0126225 A1 Apr. 23, 2020

Related U.S. Application Data

(63) Continuation of application No. PCT/JP2017/023388, filed on Jun. 26, 2017.

(51) Int. Cl.
*G06T 7/00* (2017.01)
*G02B 21/00* (2006.01)
(Continued)

(52) U.S. Cl.
CPC .......... *G06T 7/0012* (2013.01); *G02B 21/008* (2013.01); *G02B 21/365* (2013.01);
(Continued)

(58) Field of Classification Search
CPC ......... G06T 7/0012; G06T 2207/30024; G06T 2207/10056; G06T 2207/30072;
(Continued)

(56) References Cited

U.S. PATENT DOCUMENTS

| 4,907,158 A | 3/1990 | Kettler et al. |
| 2003/0081209 A1 | 5/2003 | Takahashi et al. |

(Continued)

FOREIGN PATENT DOCUMENTS

| JP | S643560 A | 1/1989 |
| JP | H08338705 A | 12/1996 |

(Continued)

OTHER PUBLICATIONS

International Search Report (ISR) dated Sep. 26, 2017 (and English translation thereof), issued in International Application No. PCT/JP2017/023393.

(Continued)

*Primary Examiner* — Vu Le
*Assistant Examiner* — Winta Gebreslassie
(74) *Attorney, Agent, or Firm* — Holtz, Holtz & Volek PC

(57) ABSTRACT

A cell observation system according to the present invention includes: a first image-acquisition device disposed in an incubator and acquires a first image of cells in a culturing vessel; a second image-acquisition device disposed outside the incubator; a processing device connected to the first and second image-acquisition devices; and a display. The second image-acquisition device includes a second image-acquisition unit that acquires a second image of the interior of the culturing vessel that removed from the incubator, a support that supports the second image-acquisition unit and the culturing vessel, and a position measuring unit that measures a position between the culturing vessel and the second image-acquisition unit at the time of acquiring the second image. The processing device extracts target cells in the first image, calculates positions of the target cells, and displays the relationship between the positions of the target cells and the second image.

13 Claims, 6 Drawing Sheets

(51) Int. Cl.
*G02B 21/36* (2006.01)
*C12M 1/00* (2006.01)
*C12M 1/34* (2006.01)

(52) U.S. Cl.
CPC ............ *C12M 41/14* (2013.01); *C12M 41/36* (2013.01); *G06T 2207/30024* (2013.01)

(58) Field of Classification Search
CPC ........... G06T 2207/10061; G06T 2207/20036; G02B 21/008; G02B 21/365; C12M 41/14; C12M 41/36
See application file for complete search history.

(56) References Cited

U.S. PATENT DOCUMENTS

| | | | |
|---|---|---|---|
| 2003/0103662 A1 | 6/2003 | Finkbeiner | |
| 2004/0152188 A1 | 8/2004 | Yamamoto et al. | |
| 2006/0115892 A1 | 6/2006 | Yamamoto et al. | |
| 2011/0013821 A1* | 1/2011 | Mimura | G06T 7/0016 382/133 |
| 2013/0027539 A1* | 1/2013 | Kiyota | C12M 41/36 348/79 |
| 2013/0309710 A1 | 11/2013 | Nakamura | |
| 2019/0339498 A1* | 11/2019 | Matsubara | G02B 21/26 |
| 2020/0110922 A1* | 4/2020 | Shinoda | C12N 5/0682 |
| 2020/0124836 A1 | 4/2020 | Miyoshi et al. | |
| 2021/0261903 A1* | 8/2021 | Blanchard | C12M 41/36 |

FOREIGN PATENT DOCUMENTS

| | | |
|---|---|---|
| JP | 2001025387 A | 1/2001 |
| JP | 2003130866 A | 5/2003 |
| JP | 2004180675 A | 7/2004 |
| JP | 2005514589 A | 5/2005 |
| JP | 2005265717 A | 9/2005 |
| JP | 2005348688 A | 12/2005 |
| JP | 2009106305 A | 5/2009 |
| JP | 2009282198 A | 12/2009 |
| JP | 2010112969 A | 5/2010 |
| JP | 2011022322 A | 2/2011 |
| JP | 2011196867 A | 10/2011 |
| JP | 2015231343 A | 12/2015 |
| WO | 2003048705 A1 | 6/2003 |
| WO | 2011089908 A1 | 7/2011 |
| WO | 2013094365 A1 | 6/2013 |
| WO | 2015107667 A1 | 7/2015 |
| WO | 2019003274 A1 | 1/2019 |

OTHER PUBLICATIONS

International Search Report (ISR) dated Sep. 5, 2017 (and English translation thereof), issued in International Application No. PCT/JP2017/023388.
Written Opinion of the International Searching Authority dated Sep. 26, 2017 issued in International Application No. PCT/JP2017/023393.
Written Opinion of the International Searching Authority dated Sep. 5, 2017 issued in International Application No. PCT/JP2017/023388.
Japanese Office Action (and English language translation thereof) dated Jun. 22, 2021 issued in Japanese Application No. 2019-526406.
Related U.S. Appl. No. 16/724,372, First Named Inventor: Takashi MIYOSHI; Title: "Cell Observation System"; filed: Dec. 22, 2019.
Notice of Termination of Reconsideration by Examiners before Appeal Proceedings (and English language translation thereof) dated Feb. 2, 2022, issued in counterpart Japanese Application No. 2019-526406.
Reconsideration Report by Examiner before Appeal (and English language translation thereof) dated Jan. 25, 2022, issued in counterpart Japanese Application No. 2019-526406.

* cited by examiner

CELL OBSERVATION SYSTEM

CROSS-REFERENCE TO RELATED APPLICATIONS

This is a continuation of International Application PCT/JP2017/023388, with an international filing date of Jun. 26, 2017, which is hereby incorporated by reference herein in its entirety.

TECHNICAL FIELD

The present invention relates to a cell observation system.

BACKGROUND ART

There is a known technology for collecting and removing target cells from a culturing vessel while observing the interior of the culturing vessel by using an observation device in a workspace such as a clean bench (for example, see Japanese Unexamined Patent Application, Publication No. 2009-106305).

SUMMARY OF INVENTION

An aspect of the present invention is a cell observation system including: a first image-acquisition device that is disposed in an incubator, the first image-acquisition device includes a first image-acquisition unit that acquires a first image of cells in a culturing vessel; a second image-acquisition device that is disposed outside the incubator, the second image-acquisition device includes a second image-acquisition unit that acquires a second image of the interior of the culturing vessel that has been removed from the incubator, a support that supports the second image-acquisition unit and the culturing vessel so as to be movable relative to each other, and a position measuring unit that measures a relative position between the culturing vessel and the second image-acquisition unit at the time of acquiring the second image; a processing device that is connected to the first image-acquisition device and the second image-acquisition device; and a display that is connected to the processing device. The processing device extracts target cells in the first image acquired by the first image-acquisition device, calculates positions at which the extracted target cells are present and stores the positions in a memory, and causes, on the basis of the relative position measured by the position measuring unit, the display to display the correspondence relationship between the positions at which the target cells are present and the position of the second image that is currently being acquired.

Another aspect of the present invention is a cell observation system including: a first image-acquisition device that is disposed in an incubator, the first image-acquisition device includes a first image-acquisition unit that acquires a first image of cells in a culturing vessel; a second image-acquisition device that is disposed outside the incubator, the second image-acquisition device includes a second image-acquisition unit that acquires a second image of the interior of the culturing vessel that has been removed from the incubator, and a support that supports the second image-acquisition unit and the culturing vessel so as to be movable relative to each other; a processing device that is connected to the first image-acquisition device and the second image-acquisition device; and a display. The processing device extracts target cells in the first image acquired by the first image-acquisition device, calculates positions at which the extracted target cells are present and stores the positions in a memory, searches for the second image in the first image by means of image matching, calculates the relative position between the culturing vessel and the second image-acquisition unit, and causes, on the basis of the calculated relative position, the display to display the correspondence relationship between the positions at which the target cells are present and the position of the second image that is currently being acquired.

DESCRIPTION OF EMBODIMENT

A cell observation system 1 according to an embodiment of the present invention will be described below with reference to the drawings.

Figure 1:
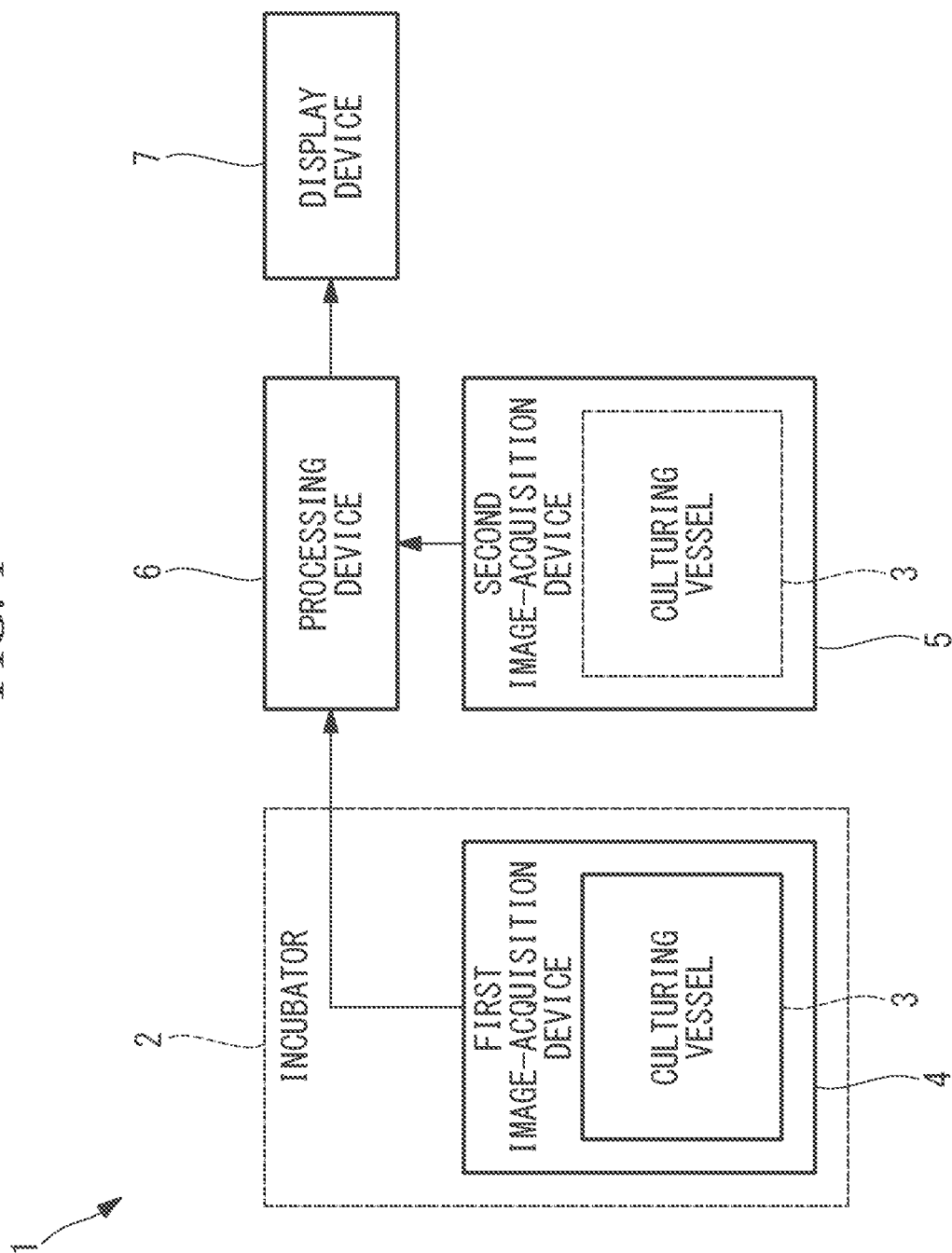
FIG. 1 FIG. 1 is a block diagram showing a cell observation system according to an embodiment of the present invention.

As shown in FIG. 1, the cell observation system 1 according to this embodiment includes: a first image-acquisition device 4 that is disposed in an incubator 2 for culturing cells (see FIG. 5) X, that has a culturing vessel 3 seeded with the cells X placed thereon, and that acquires a first image of the cells X in the culturing vessel 3; a second image-acquisition device 5 that is disposed outside the incubator 2, that has the culturing vessel 3 that has been removed from the incubator 2 placed thereon, and that acquires a second image of the cells X in the culturing vessel 3; a processing device 6 that is connected to the first image-acquisition device 4 and the second image-acquisition device 5; and a display 7 that is connected to the processing device 6.

Figure 2:
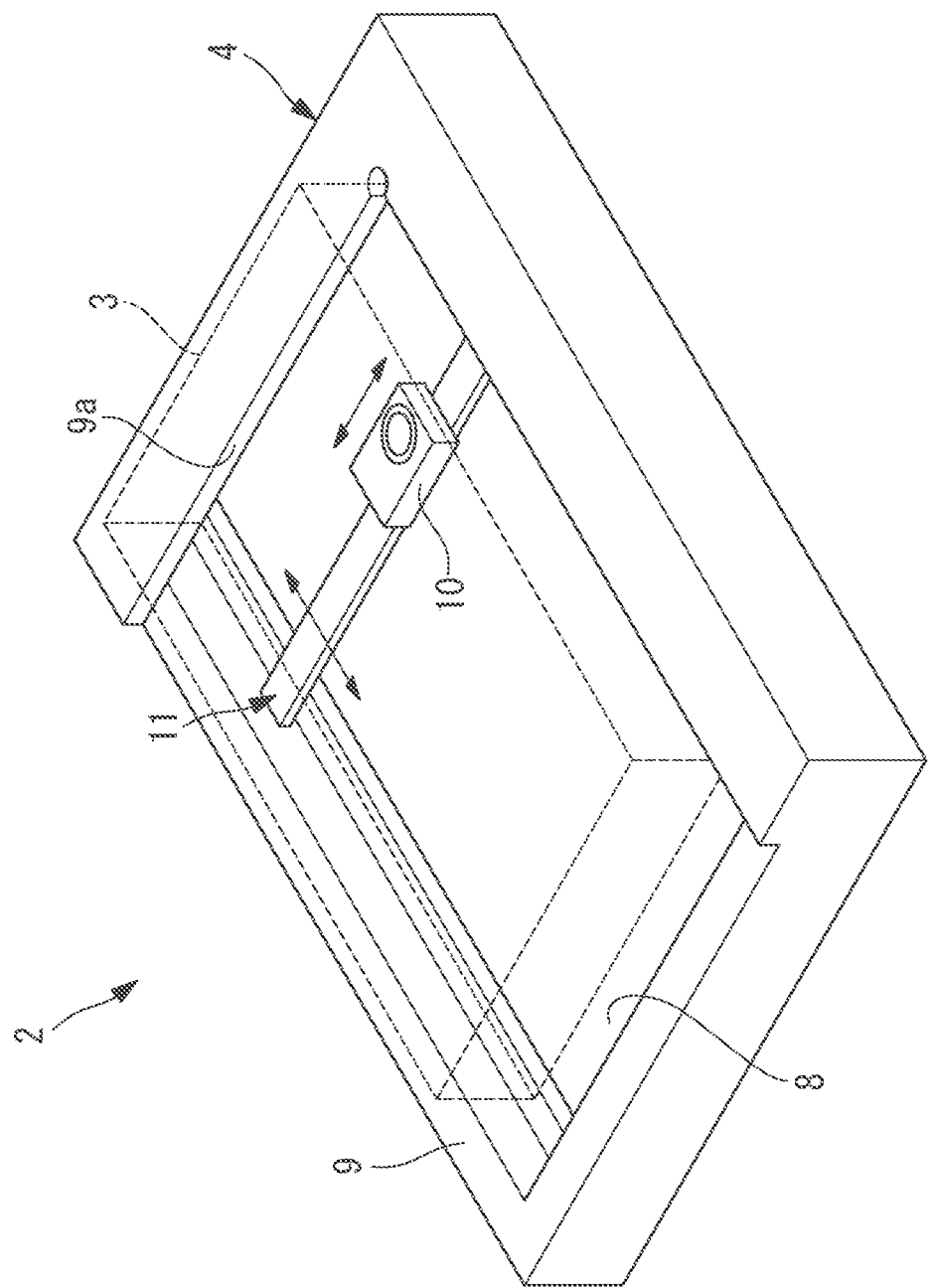
FIG. 2 FIG. 2 is a plan view showing a first image-acquisition device provided in the cell observation system in FIG. 1.

As shown in FIG. 2, the first image-acquisition device 4 includes: a stage 9 on which the culturing vessel 3 having at least a bottom surface made of an optically transparent material is placed, and that has a window 8 that is at least partially transparent; a first image-acquisition unit 10 that captures images of the cells X in the culturing vessel 3 placed on the stage 9 from below the stage 9; and a driving unit 11 that moves the first image-acquisition unit 10 in two horizontal directions with respect to the stage 9.

The culturing vessel 3 is, for example, a multiwell plate that has a rectangular external shape and that has six wells arranged in two rows and three columns.

The stage 9 includes two abutting surfaces 9a against which two adjacent side surfaces of the culturing vessel 3 placed on the stage 9 are abutted, and, as a result of individually abutting the two side surfaces of the culturing vessel 3 against the two abutting surfaces 9a, it is possible to place the culturing vessel 3 in a positioned state.

The first image-acquisition unit 10 is a camera that includes a required optical system such as a focusing lens, and is provided with a field of view that is sufficiently smaller than the bottom surface of the culturing vessel 3.

The driving unit 11 includes, for example: a motor; a slider on which the first image-acquisition unit 10 is placed; and two linear motion mechanisms that convert the motive power of the motor into the motions of the slider in two horizontal directions, although these components are not illustrated. The motor includes an encoder, and thus, it is possible to detect the position (relative position) of the first image-acquisition unit 10 in the horizontal direction when the driving unit 11 is operated, assuming that the first image-acquisition unit 10 is at the origin in the state in which the optical axis of the first image-acquisition unit 10 is disposed at a prescribed position with respect to the intersection of the two abutting surfaces 9a.

By doing so, the first image-acquisition device 4 transmits, to the processing device 6, the images (partial images) acquired by the first image-acquisition unit 10 as a result of moving the first image-acquisition unit 10 to the prescribed position by causing the driving unit 11 to be driven and the position of the first image-acquisition unit 10 detected by the encoder at that time, in association with each other.

Figure 3:
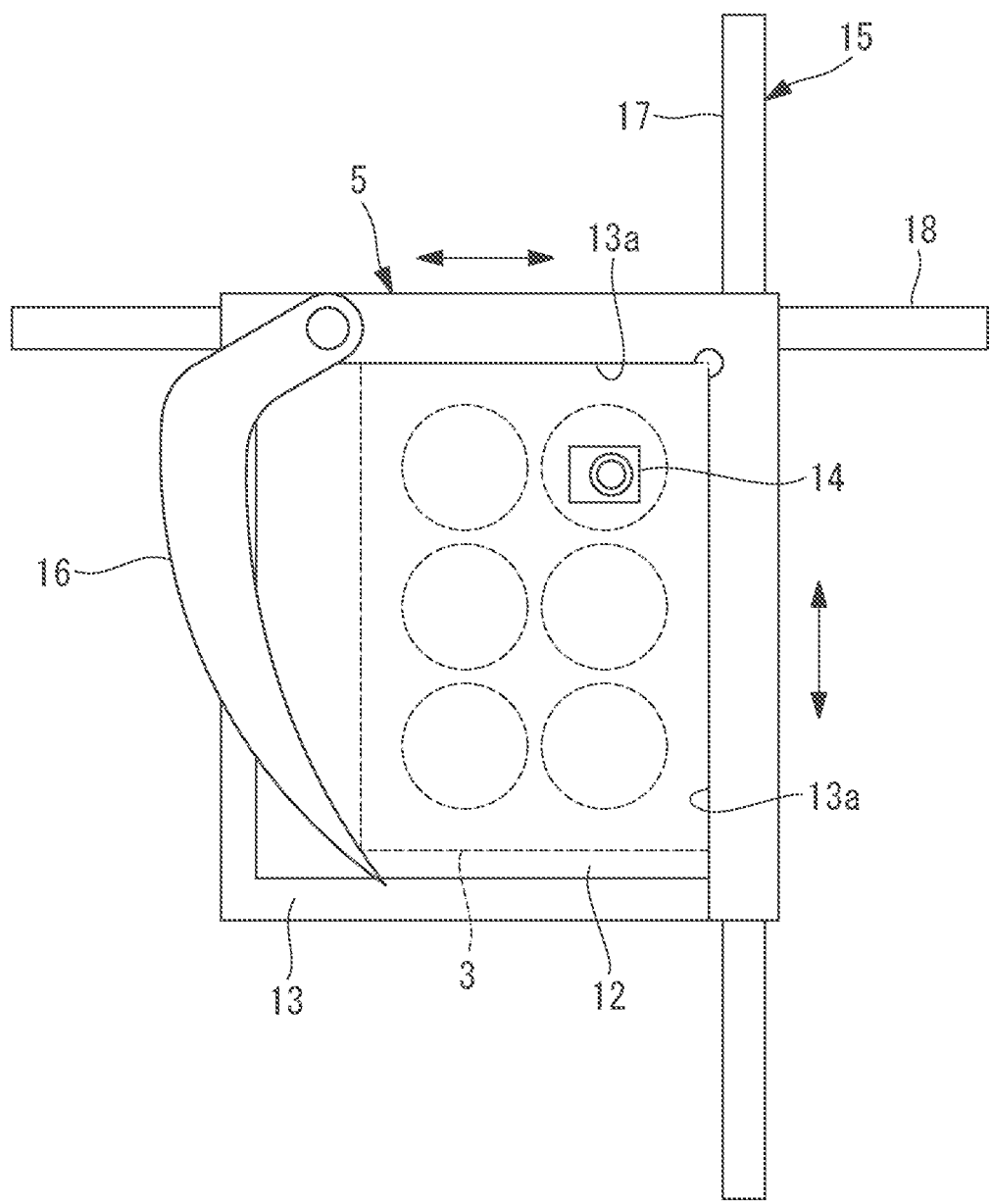
FIG. 3 FIG. 3 is a plan view showing a second image-acquisition device provided in the cell observation system in FIG. 1.

As shown in FIG. 3, the second image-acquisition device 5 includes: a slide stage 13 that has a window 12 that is at least partially transparent; a second image-acquisition unit 14 that is disposed below the slide stage 13 and that captures images of the cells X in the culturing vessel 3 placed on the slide stage 13; and a support 15 that supports the slide stage 13 so as to be movable in two horizontal directions.

The second image-acquisition unit 14 is a camera that includes a required optical system such as a focusing lens, and has a magnification that is lower than that of the first image-acquisition unit 10 or a magnification that is equivalent to that of the first image-acquisition unit 10. The first image-acquisition unit 10 may be configured so as to be switched to a higher magnification for performing a detailed check.

The slide stage 13 includes: two abutting surfaces 13a against which two adjacent side surfaces of the culturing vessel 3 placed on the slide stage 13 are abutted; and a vessel clamp 16 that, as a result of sandwiching the culturing vessel 3 between the vessel clamp 16 and the two abutting surfaces 13a, secures the culturing vessel 3 to the slide stage 13 in a positioned state. The vessel clamp 16 is biased, by means of a spring (not shown), in a direction in which the distances between the vessel clamp 16 and the two abutting surfaces 13a are reduced.

The support 15 includes: guide rails 17 and 18 that guide the slide stage 13 in two directions that are orthogonal to each other; and an encoder (position measuring unit (not shown)) that detects the amount of movement of the slide stage 13 when the slide stage 13 is moved along the respective guide rails 17 and 18. The encoder may be a linear scale, or may be of a rotational type that detects the amount of linear movement of the slide stage 13 by means of conversion to a rotational angle.

In the second image-acquisition device 5, the relative positional relationship between the optical axis of the second image-acquisition unit 14 and the intersection of the two abutting surfaces 13a of the slide stage 13 when the second image-acquisition unit 14 is disposed at the origin is set so as to be equal to the relative positional relationship between the optical axis of the first image-acquisition unit 10 and the intersection between the two abutting surfaces 13a of the slide stage 13 when the first image-acquisition unit 10 is disposed at the origin in the first image-acquisition device 4.

By doing so, by moving the slide stage 13 after securing the culturing vessel 3 to the slide stage 13, the second image-acquisition device 5 transmits, to the processing device 6, the images acquired by the second image-acquisition unit 14 and the positions of the slide stage 13 detected by the encoder at that time, in association with each other.

The processing device 6 includes a one or more processors and a memory that are not illustrated. By means of the processor, the processing device 6 receives the plurality of images transmitted from the first image-acquisition device 4 and the positions of the first image-acquisition unit 10 at the time of acquiring the respective images, generates a larger first image in which the plurality of images are combined, and processes the generated first image, thus extracting target cells.

It is possible to extract the target cells as cells differing from the other cells X, for example, by calculating shape features of the cells X. The processing device 6 stores, for example, the center-of-gravity positions of the extracted target cells in the memory as the positions of the target cells.

Figure 4:
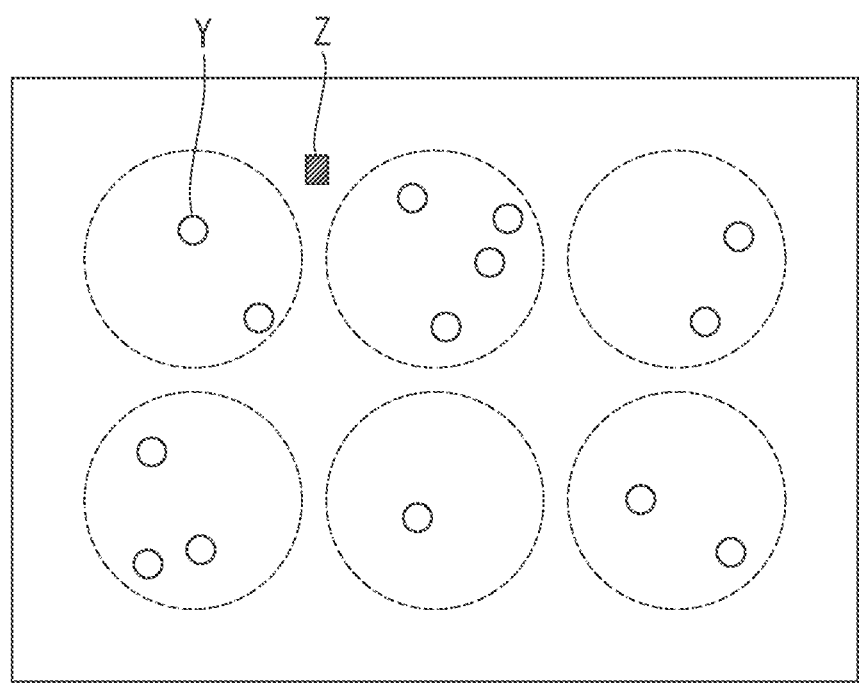
FIG. 4 FIG. 4 is a diagram showing an example of a well guide to be displayed on a display of the cell observation system in FIG. 1.

Then, as shown in FIG. 4, after completing extraction of the target cells in all regions in the first image, the processing device 6 generates marks Y, which indicate positions at which the target cells are present, in a well guide superimposed on a vessel-dimension image representing the culturing vessel 3.

The processing device 6 generates a rectangular frame Z, which indicates the position of a second image, in the well guide on the basis of the position of the second image transmitted from the second image-acquisition device 5, as shown in FIG. 4.

Figure 5:
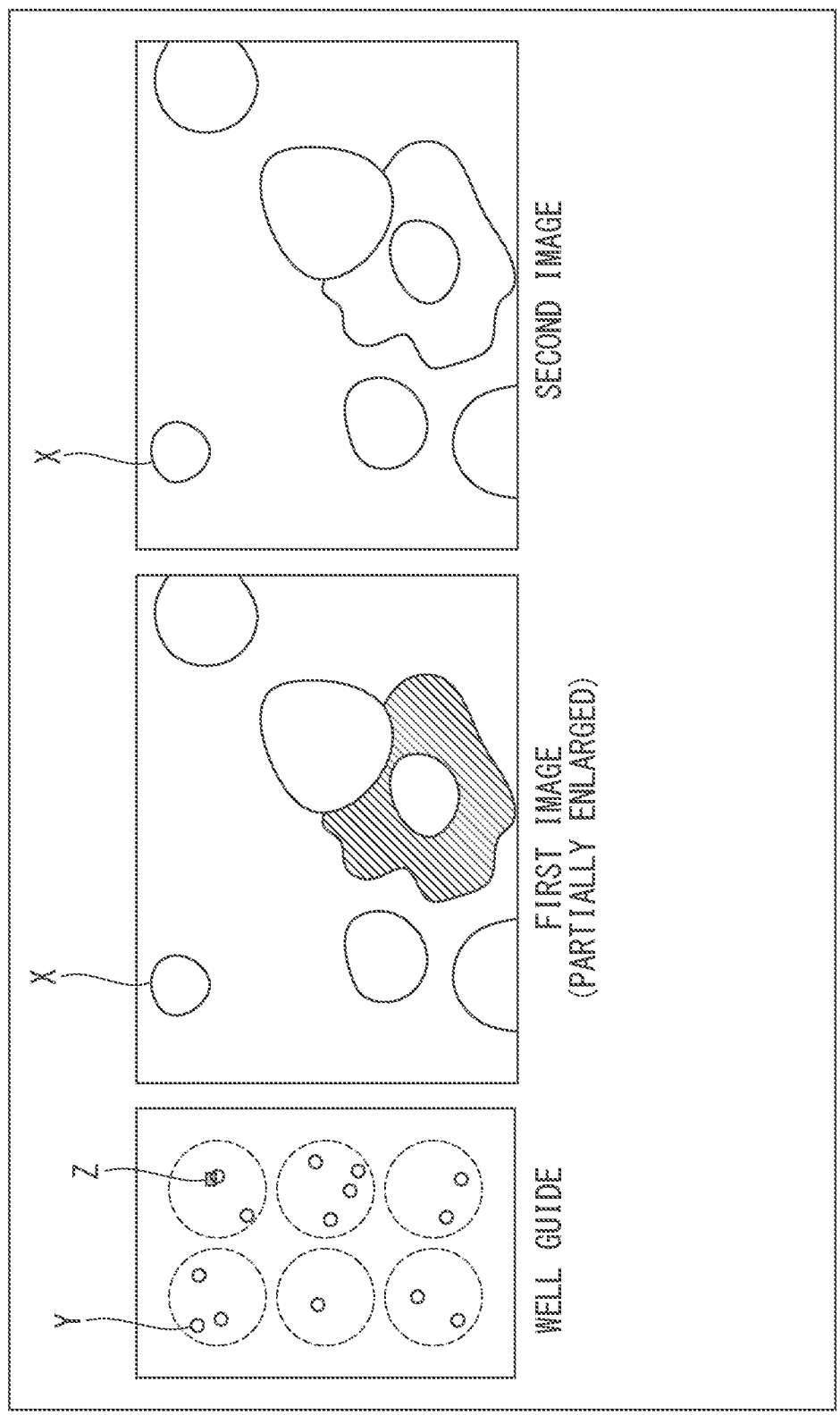
FIG. 5 FIG. 5 is a diagram showing a display example in the display of the cell observation system in FIG. 1.

Furthermore, the processing device 6 causes the display 7 to display, next to each other, the well guide on which the frame Z indicating the second image is superimposed, the second image itself, and a region of the first image that has the same position as the second image and that has the same size as the second image, as shown in FIG. 5. In the figure, the hatched region in the first image indicates a target cell.

Because the position in the culturing vessel 3 being captured by the second image-acquisition unit 14 changes when the user moves the culturing vessel 3 in the horizontal direction in the second image-acquisition device 5, the frame Z moves in the well guide, and the second image and the image of the region of the first image change in real time.

The operation of the cell observation system 1 according to this embodiment, thus configured, will be described below.

In order to observe the cells X by using the cell observation system 1 according to this embodiment, the culturing vessel 3 accommodating the cells X and a medium is placed on the stage 9 of the first image-acquisition device 4 in the incubator 2, and two adjacent side surfaces of the culturing vessel 3 are abutted against the two abutting surfaces 9a provided in the stage 9. By doing so, the culturing vessel 3 is placed on the stage 9 in a positioned state.

In this state, the cells X that grow adhering to the bottom surface of the culturing vessel 3 are cultured while managing the interior of the incubator 2 so as to be at prescribed temperature and humidity. Then, for example, when the time for passaging the cells X is reached, the first image-acquisition device 4 is operated, a plurality of partial images of the cells X adhered to the bottom surface of the culturing vessel 3 are acquired, the positions of the optical axis of the first image-acquisition unit 10 at the time of acquiring the respective partial images are associated with the reference position of the stage 9, and this information is transmitted to the processing device 6 in association of the partial images.

The processing device 6 generates a first image having a greater angle of view by combining the plurality of partial images transmitted thereto, and performs processing in which target cells are extracted in the generated first image. Examples of the target cells include cells X determined to be cells that should be isolated or discarded by using a pipette or an aspirator as a result of distinguishing the colony states of the cells X.

As shown in FIG. 4, the processing device 6 generates a well guide that represents the shape of the culturing vessel 3, and superimposes, for example, circular marks Y at the positions extracted as being the target cells.

The user removes the culturing vessel 3 from the incubator 2, and places the culturing vessel 3 on the slide stage 13 of the second image-acquisition device 5 disposed in a clean bench outside the incubator 2. Then, the two side surfaces of the culturing vessel 3 are abutted against the two abutting surfaces 13a provided in the slide stage 13, and the culturing vessel 3 is secured on the slide stage 13 by means of the vessel clamp 16.

Because the relative position of the slide stage 13 with respect to the second image-acquisition unit 14 is measured by the encoder, the processing device 6 generates the frame Z, which indicates the position of the second image, on the well guide in a superimposed manner.

The display 7 displays the well guide generated by the processing device 6, the first image acquired by the first image-acquisition unit 10, and the second image acquired by the second image-acquisition unit 14.

As a result of the user moving the culturing vessel 3 in the horizontal direction with respect to the second image-acquisition unit 14 by operating the slide stage 13 of the second image-acquisition device 5 while viewing the well guide, the frame Z is moved on the well guide in synchronization with the movement of the culturing vessel 3; therefore, it is possible to move the culturing vessel 3 so that the frame Z, which indicates the position of the second image-acquisition unit 14, is aligned with a circular mark Y, which indicates the position of an extracted target cell.

Also, because the display 7 displays the first image and the second image at the position corresponding to the frame Z next to the well guide, it is possible to perform observation by comparing the first image acquired in the incubator 2 and the second image that is currently being acquired outside the incubator 2.

Because the first image and the second image containing the target cell are displayed when the frame Z is aligned with one of the circular marks Y, the user can isolate the target cell by means of a pipette or the like, and he/she can perform observation by comparing the first image before the isolation and the second image after the isolation.

As has been described above, with the cell observation system 1 according to this embodiment, the target cells are extracted by processing the first image acquired in the incubator 2, and the positions of the extracted target cells are displayed outside the incubator 2; therefore, the user can easily confirm the target cells by aligning the second image-acquisition unit 14 with the displayed positions, and he/she can quickly perform treatment such as isolation or the like.

Therefore, there is an advantage in that, as a result of reducing the time and effort for the user to search for the target cells, it is possible to find the target cells in the culturing vessel 3 in a comprehensive manner.

As a result, because it is not necessary to search for the target cells after removal from the incubator 2, it is possible to prevent the cells X from being exposed, for a long time, to a situation in which a culturing environment is not prepared, and thus, it is possible to maintain the cells X in a healthy state.

Note that, in this embodiment, although the circular marks Y indicating the target cells are superimposed on the well guide indicating the culturing vessel 3, in addition thereto, the first image acquired by the first image-acquisition device 4 may be displayed in a superimposed manner. By doing so, the user can confirm the positions of the target cells while viewing the entire first image, and thus, he/she can more intuitively confirm the target cells.

In this embodiment, when the processing device 6 causes the display 7 to display the first image, the extracted target cells may be displayed in an emphasized manner. Examples of the emphasized display include adding a color differing from the color of other regions. Specifically, as a result of the target cells displayed in the first image being displayed in an emphasized manner when the target cells are brought into the field of view of the second image-acquisition unit 14 by operating the slide stage 13, it is possible to more easily confirm the target cells.

In this embodiment, although the frame Z, which indicates the position of the second image, is displayed on the well guide in a superimposed manner, in addition thereto, a frame Z that represents the second image-acquisition unit 14 may be displayed in a superimposed manner. As a result of superimposing the frame Z, which represents the second image-acquisition unit 14, on the well guide, which represents the culturing vessel 3, it is possible to display the relationship between the culturing vessel 3 and the second image-acquisition unit 14 on the second image-acquisition device 5 in a manner that is closer to reality, and thus, the user can more intuitively operate the slide stage 13.

In this embodiment, although the second image-acquisition device 5 is provided with the encoder that measures the relative position between the slide stage 13 and the second image-acquisition unit 14, alternatively, the relative position between the slide stage 13 and the second image-acquisition unit 14 may be estimated by means of image processing without providing a position measuring unit such as an encoder. Specifically, the second image acquired by the second image-acquisition unit 14 may be searched for in the first image by performing image matching. By doing so, it is possible to identify the position of the optical axis of the second image-acquisition unit 14 with respect to the culturing vessel 3 in the first image, and, similarly, it is possible to display the position of the second image-acquisition unit 14 on the well guide in a superimposed manner.

Figure 6:
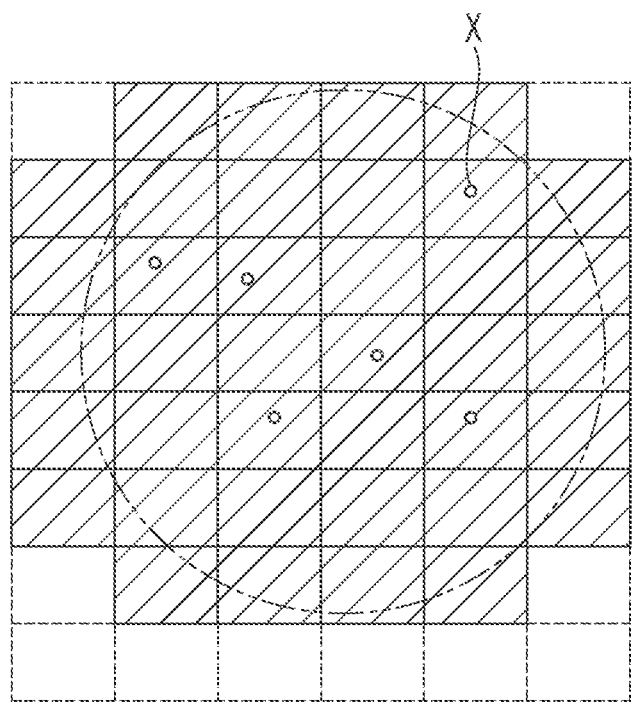
FIG. 6 FIG. 6 is a diagram showing a first image generated by a modification of the cell observation system in FIG. 1.

Although a plurality of partial images are acquired as first images, and a first image is generated by the processing device 6 by combining the partial images, alternatively, a single first image may be captured once by a first image-acquisition unit 10 having a low magnification. As shown in FIG. 6, the first image may be generated in the form of an image consisting only of partial images of regions in which the cells X are present, that is, regions in the culturing vessel 3 in which the cells X are accommodated, for example, bottom surfaces of the wells, and, in the image, regions of members between the wells and regions other than the bottom surface of the culturing vessel 3 may be blank.

As a result, the following aspect is read from the above described embodiment of the present invention.

An aspect of the present invention is a cell observation system including: a first image-acquisition device that is disposed in an incubator, the first image-acquisition device includes a first image-acquisition unit that acquires a first image of cells in a culturing vessel; a second image-acquisition device that is disposed outside the incubator, the second image-acquisition device includes a second image-acquisition unit that acquires a second image of the interior of the culturing vessel that has been removed from the incubator, a support that supports the second image-acquisition unit and the culturing vessel so as to be movable relative to each other, and a position measuring unit that measures a relative position between the culturing vessel and the second image-acquisition unit at the time of acquiring the second image; a processing device that is connected to the first image-acquisition device and the second image-acquisition device; and a display that is connected to the processing device. The processing device extracts target cells in the first image acquired by the first image-acquisition device, calculates positions at which the extracted target cells are present and stores the positions in a memory, and causes, on the basis of the relative position measured by the position measuring unit, the display to display the correspondence relationship between the positions at which the target cells are present and the position of the second image that is currently being acquired.

With this aspect, when the culturing vessel seeded with the cells is accommodated in the first image-acquisition device disposed in the incubator, and the first image of the cells in the culturing vessel is acquired by the first image-acquisition unit, the acquired first image is transmitted to the processing device, the target cells in the first image are extracted, and the positions at which the target cells are present are calculated and stored.

When the culturing vessel and the second image-acquisition unit are moved relative to each other after removing the culturing vessel from the incubator and causing the support of the second image-acquisition device disposed outside the incubator to support the culturing vessel, the second image is acquired by the second image-acquisition unit, and the relative position is measured by the position measuring unit.

The processing device causes the display to display the correspondence relationship between the positions of the target cells extracted in the first image and the position of the second image that is currently being acquired.

The user moves the culturing vessel and the second image-acquisition unit relative to each other while viewing the correspondence relationship displayed on the display, aligns the field of view of the second image-acquisition unit with the positions at which the target cells are present, and thus, he/she can display the second image containing the target cells on the display. Thus, by doing so, it is possible to find the target cells in a comprehensive, effective manner in a workspace such as a clean bench.

In the above-described aspect, the position measuring unit may be an encoder that measures the relative position between the culturing vessel and the second image-acquisition unit in two horizontal directions with reference to a reference position of the culturing vessel.

By doing so, when the user places the culturing vessel that has been removed from the incubator in the support, and moves the culturing vessel and the second image-acquisition unit relative to each other, the relative position between the two with reference to the reference position of the culturing vessel is measured by the encoder.

Another aspect of the present invention is a cell observation system including: a first image-acquisition device that is disposed in an incubator, the first image-acquisition device includes a first image-acquisition unit that acquires a first image of cells in a culturing vessel; a second image-acquisition device that is disposed outside the incubator, the second image-acquisition device includes a second image-acquisition unit that acquires a second image of the interior of the culturing vessel that has been removed from the incubator, and a support that supports the second image-acquisition unit and the culturing vessel so as to be movable relative to each other; a processing device that is connected to the first image-acquisition device and the second image-acquisition device; and a display that is connected to the processing device. The processing device extracts target cells in the first image acquired by the first image-acquisition device, calculates positions at which the extracted target cells are present and stores the positions in a memory, searches for the second image in the first image by means of image matching, calculates the relative position between the culturing vessel and the second image-acquisition unit, and causes, on the basis of the calculated relative position, the display to display the correspondence relationship between the positions at which the target cells are present and the position of the second image that is currently being acquired.

With this aspect, when the culturing vessel seeded with the cells is accommodated in the first image-acquisition device disposed in the incubator, and the first image of the cells in the culturing vessel is acquired by the first image-acquisition unit, the acquired first image is transmitted to the processing device, the target cells in the first image are extracted, and the positions at which the target cells are present are calculated and stored.

When the culturing vessel and the second image-acquisition unit are moved relative to each other after removing the culturing vessel from the incubator and causing the support of the second image-acquisition device disposed outside the incubator to support the culturing vessel, the processing device searches for the second image acquired by the second image-acquisition unit in the first image by means of image matching, and the relative position between the culturing vessel and the second image-acquisition unit is calculated.

The processing device causes the display to display the correspondence relationship between the positions of the target cells extracted in the first image and the position of the second image that is currently being acquired.

The user moves the culturing vessel and the second image-acquisition unit relative to each other while viewing the correspondence relationship displayed on the display, aligns the field of view of the second image-acquisition unit with the positions at which the target cells are present, and thus, he/she can display the second image containing the target cells on the display. Thus, by doing so, it is possible to find the target cells in a comprehensive, effective manner in a workspace such as a clean bench.

In the above-described aspect, the first image-acquisition unit may acquire a plurality of partial images that constitute the first image, and the first image-acquisition device may include a driving unit that moves the first image-acquisition unit and the culturing vessel relative to each other, and may transmit, to the processing device, the individual partial images and the relative positions between the cultural vessel and the first image-acquisition unit at the time of acquiring the partial images, in association with each other.

By doing so, the first image-acquisition unit acquires the plurality of partial images of the cells in the culturing vessel, and transmits, to the processing device, the individual partial images in association with the relative positions between the culturing vessel and the first image-acquisition unit at the time of acquiring the respective partial images. By doing so, it is possible to generate, in the processing device, a first image having a greater size than the field of view of the first image-acquisition unit.

In the above-described aspect, the processing device may generate a vessel-dimension image that represents the culturing vessel and may cause the vessel-dimension image to be displayed, and may cause the position of the second image to be displayed on the vessel-dimension image in a superimposed manner.

By doing so, it is possible to select, while viewing the vessel-dimension image displayed on the display, the positions at which target cells are present, which are displayed in a superimposed manner.

In the above-described aspect, the processing device may cause the display to display the first image on the vessel-dimension image in a superimposed manner.

By doing so, it is possible to select, while viewing the first image displayed on the display, the positions at which target cells are present, which are displayed in a superimposed manner.

In the above-described aspect, the processing device may cause the extracted target cells to be displayed on the first image in an emphasized manner.

By doing so, as a result of the target cells being displayed in an emphasized manner when the first image containing the target cells is displayed, it is possible to easily identify the positions of the target cells.

REFERENCE SIGNS LIST 1 cell observation system
2 incubator
3 culturing vessel
4 first image-acquisition device
5 second image-acquisition device
6 processing device
7 display
10 first image-acquisition unit
11 driving unit
14 second image-acquisition unit
15 support
X cell

The invention claimed is:

1. A cell observation system comprising:
an incubator;
a first image-acquisition device disposed in the incubator, the first image-acquisition device comprising:
a first imager configured to acquire a first image of cells in a culturing vessel; and
a driver configured to move the first imager relative to a first stage on which the culturing vessel is placed,
a second image-acquisition device disposed outside the incubator, the second image-acquisition device comprising:
a second imager configured to acquire a second image of an interior of the culturing vessel, which has been removed from the incubator;
a support configured to movably support a second stage on which the culturing vessel is placed such that the second stage is movable relative to the second imager, the second stage being separate from the first stage, and
a position measurer configured to measure a relative position between the culturing vessel and the second imager at a time of acquiring the second image;
a processing device connected to the first image-acquisition device and the second image-acquisition device; and
a display connected to the processing device,
wherein;
the processing device comprises at least one processor and a memory,
the first image includes a plurality of partial images acquired by the first imager,
the first image-acquisition device, at a time of acquiring each partial image included in the first image, detects a relative position between the culturing vessel and the first imager and associates the partial image with the detected relative position, and
the at least one processor is configured to:
extract target cells in the first image, which is constituted from the partial images, acquired by the first image-acquisition device,
calculate positions at which the extracted target cells are present and store the positions in the memory, and
cause, based on (i) the relative position measured by the position measurer and (ii) the relative position between the culturing vessel and the first imager detected by the first image-acquisition device, the display to display a correspondence relationship between the positions at which the target cells are present and the position of the second image that is currently being acquired.

2. The cell observation system according to claim 1, wherein:
the position measurer comprises an encoder, and
the encoder is configured to measure the relative position between the culturing vessel and the second imager in two horizontal directions with reference to a reference position of the culturing vessel.

3. A cell observation system comprising:
an incubator;
a first image-acquisition device disposed in the incubator, the first image-acquisition device comprising:
a first imager configured to acquire a first image of cells in a culturing vessel; and
a driver configured to move the first imager relative to a first stage on which the culturing vessel is placed,
a second image-acquisition device disposed outside the incubator, the second image-acquisition device comprising:
a second imager configured to acquire a second image of an interior of the culturing vessel, which has been removed from the incubator; and
a support configured to support the second imager and the culturing vessel such that the second imager and the culturing vessel are movable relative to each other, the support being separate from the driver;
a processing device connected to the first image-acquisition device and the second image-acquisition device; and
a display connected to the processing device,
wherein;
the processing device comprises at least one processor and a memory,
the first image includes a plurality of partial images acquired by the first imager,
the first image-acquisition device, at a time of acquiring each partial image included in the first image, detects a relative position between the culturing vessel and the first imager and associates the partial image with the detected relative position, and the at least one processor is configured to:

extract target cells in the first image, which is constituted from the partial images, acquired by the first image-acquisition device, calculate positions at which the extracted target cells are present and store the positions in the memory, search for the second image in the first image by performing image matching, and cause, based on the detected relative position, the display to display a correspondence relationship between the positions at which the target cells are present and the position of the second image that is currently being acquired.

4. The cell observation system according to claim 1, wherein the first image-acquisition device transmits, to the processing device, the individual partial images and the relative positions between the culturing vessel and the first imager at the time of acquiring the partial images, in association with each other.

5. The cell observation system according to claim 1, wherein the at least one processor is configured to:

generate a vessel-dimension image that represents the culturing vessel, and cause the display to display the vessel-dimension image, and cause the display to display the position of the second image on the vessel-dimension image in a superimposed manner.

6. The cell observation system according to claim 5, wherein the at least one processor is configured to control the display to display the first image on the vessel-dimension image in a superimposed manner.

7. The cell observation system according to claim 1, wherein the at least one processor is configured to control the display to display the extracted target cells on the first image in an emphasized manner.

8. The cell observation system according to claim 3, wherein the first image-acquisition device transmits, to the processing device, the individual partial images and the relative positions between the culturing vessel and the first imager at the time of acquiring the partial images, in association with each other.

9. The cell observation system according to claim 3, wherein the at least one processor is configured to:

generate a vessel-dimension image that represents the culturing vessel, and cause the display to display the vessel-dimension image, and cause the display to display the position of the second image on the vessel-dimension image in a superimposed manner.

10. The cell observation system according to claim 9, wherein the at least one processor is configured to control the display to display the first image on the vessel-dimension image in a superimposed manner.

11. The cell observation system according to claim 3, wherein the at least one processor is configured to control the display to display the extracted target cells on the first image in an emphasized manner.

12. The cell observation system according to claim 1, wherein the at least one processor is configured to generate and display marks indicating the positions at which the target cells are present and a mark indicating the position of the second image that is currently being acquired.

13. The cell observation system according to claim 3, wherein the at least one processor is configured to generate and display marks indicating the positions at which the target cells are present and a mark indicating the position of the second image that is currently being acquired.

* * * * *